United States Patent [19]

Soloman

[11] Patent Number: 5,679,954
[45] Date of Patent: Oct. 21, 1997

[54] NON-DESTRUCTIVE IDENTIFICATION OF TABLET AND TABLET DISSOLUTION BY MEANS OF INFARED SPECTROSCOPY

[76] Inventor: Sabrie Soloman, 31 N. Monroe St., Ridgewood, N.J. 07450

[21] Appl. No.: 338,909

[22] Filed: Nov. 14, 1994

[51] Int. Cl.[6] .................. G01J 3/00; G01J 5/08; G01J 5/18
[52] U.S. Cl. .................. 250/339.08; 250/339.12; 250/339.11
[58] Field of Search .................. 250/339.08, 339.12, 250/339.11, 368, 339.07

[56] References Cited

U.S. PATENT DOCUMENTS

| | | |
|---|---|---|
| 4,384,206 | 5/1983 | Bjarno .................. 250/339 |
| 4,841,145 | 6/1989 | Wada et al. .................. 250/304 |
| 4,980,292 | 12/1990 | Elbert et al. .................. 435/289 |
| 5,008,666 | 4/1991 | Gebert et al. .................. 340/936 |
| 5,089,701 | 2/1992 | Dull et al. .................. 250/339.08 |
| 5,160,826 | 11/1992 | Cohen et al. .................. 250/339 |
| 5,171,995 | 12/1992 | Gast et al. .................. 250/339 |
| 5,262,644 | 11/1993 | Maguire .................. 250/339.08 |

Primary Examiner—Michael J. Tokar
Assistant Examiner—Virgil O. Tyler
Attorney, Agent, or Firm—Kane, Dalsimer, Sullivan, Kurucz, Levy, Eisele and Richard, LLP

[57] ABSTRACT

An automatic non-destructive real time infrared system includes special bundle of fiber optics having the ability to convey infrared light waves to solid organic-base compounds and receive reflected infrared light waves from the same. A sample of manufactured solid compound of organic-base is conveyed by mechanical and pneumatic means to a holding receptacle located under the field of view of the fiber optics probe. The probe is directly linked to a spectrophotometer to obtain a spectrum. The spectrophotometer is linked to a computer system determining the exact dissolution measurement of each manufactured solid organic-base compound. The compacted solid of organic-base compound is released from the receptacle by an ejection means to be dispensed in a holding container for storage. The storage container maintains the sample sequence. A new sample is dispensed to the holding receptacle allowing for new measurement of dissolution.

21 Claims, 16 Drawing Sheets

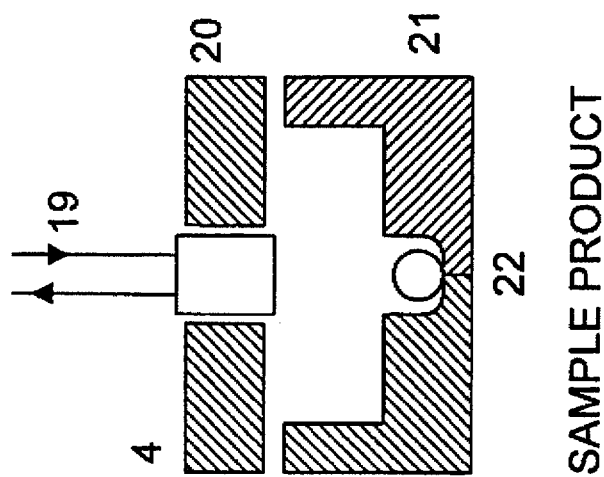
F I G. 4
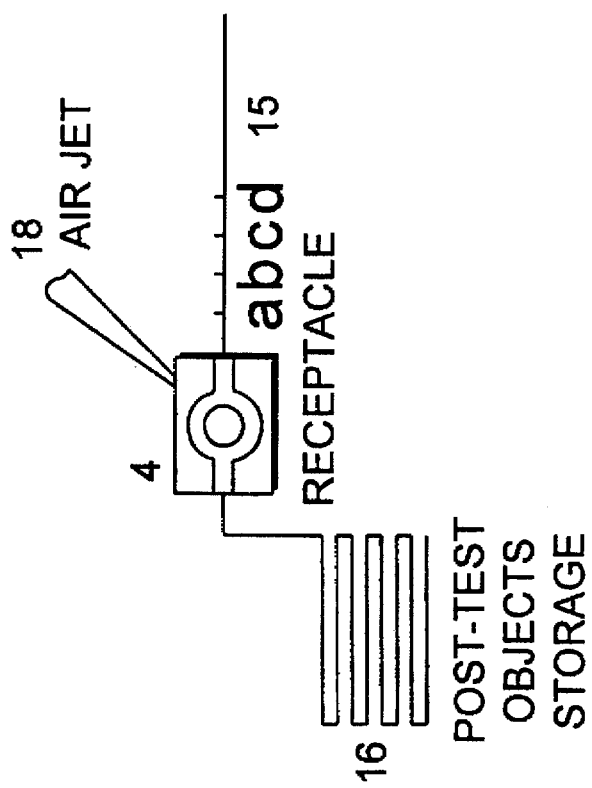
F I G. 3

NON-DESTRUCTIVE IDENTIFICATION OF TABLET AND TABLET DISSOLUTION BY MEANS OF INFARED SPECTROSCOPY

BACKGROUND OF INVENTION

The present invention is directed to an infrared spectrophotometer system. Such systems have utility in various fields, including the application of dissolution through hardness measurements, such as in pharmaceutical industry. It is desirable that such a system should be adaptable to mass production techniques so that tablets and solid organic-base compounds could be analyzed at high speed. It would also be desirable if such a system could effectively operate without the need for complicated chemical analysis and complicated chemometeric tools. Ideally such a system should incorporate safety mechanisms to automatically turn off the production system when an unsafe condition is detected. Additionally, such a system should have the capability of sensing errors in the system, such as missing compound, missing potency, or excessive presence of compound occur.

SUMMARY OF INVENTION

An object of this invention is to provide an automatic non-destructive near infrared spectroscopic measurement of dissolution which fulfills the above needs.

A further object of this invention is to provide such a system which has a particular utility for tablet dissolution, such as used in the pharmaceutical industry.

In accordance with this invention, the automatic near infrared spectroscopy system for measuring tablet dissolution through hardness includes a probe, with fiber optics bundle, connected to a near infrared spectrophotometer analyzing energy passing through the fiber optics bundle directed at the resting tablet in the holding receptacle. A plurality of pre-coated tablets departing their forming cavities fall into a holding drum. A sample tablet departing its cavity is conveyed to the receptacle instead of falling into the holding drum via a diverting mechanism which is activated periodically. The presence of the pre-coated tablet in the receptacle shuts off the diverting mechanism preventing any tablet to be conveyed to the receptacle. When the pre-coated tablet is secured in the receptacle a beam of near infrared light waves is energized, passed through the fiber optics bundle, and reflected back to the same fiber optics bundle to be passed again to the spectrophotometer for a certain period of time during which a tablet spectrum is generated. The tested pre-coated tablets are automatically removed from the receptacle in a way allowing them to be stored in the proper sequence to correspond with their acquired data.

In a preferred practice of the invention, the testing of the pre-coated tablets, departing from the supply station, is synchronized with their perspective forming cavities. The system preferably also includes a feedback signal generated by the computer to stop the tableting supply station when the dissolution measurement reaches an unacceptable value. The system preferably also includes an air ejection mechanism to remove the pre-coated tablets from the receptacle once the dissolution test is completed, allowing it to be stored in the proper sequence corresponding with the acquired data.

Sensors may be located suitably positioned for determining various conditions, such as the presence and absence of the tablets in the receptacle, correspondence of tablets with their forming cavities, and correspondence of the spectrum of tablet dissolution with each tablet and its cavity.

THE DRAWING

FIG. 3 is a top plan view of a portion of the system in FIG. 1 depicting the tablet conveying mechanism to the receptacle of the infrared fiber optics sensor which leads to post-test objects storage;

FIG. 4 is a partly sectional side view of the system shown in FIG. 1 depicting the receptacle holding one end of the infrared fiber optics sensor aimed at a tablet to be tested;

DETAILED DESCRIPTION

Figure 1:
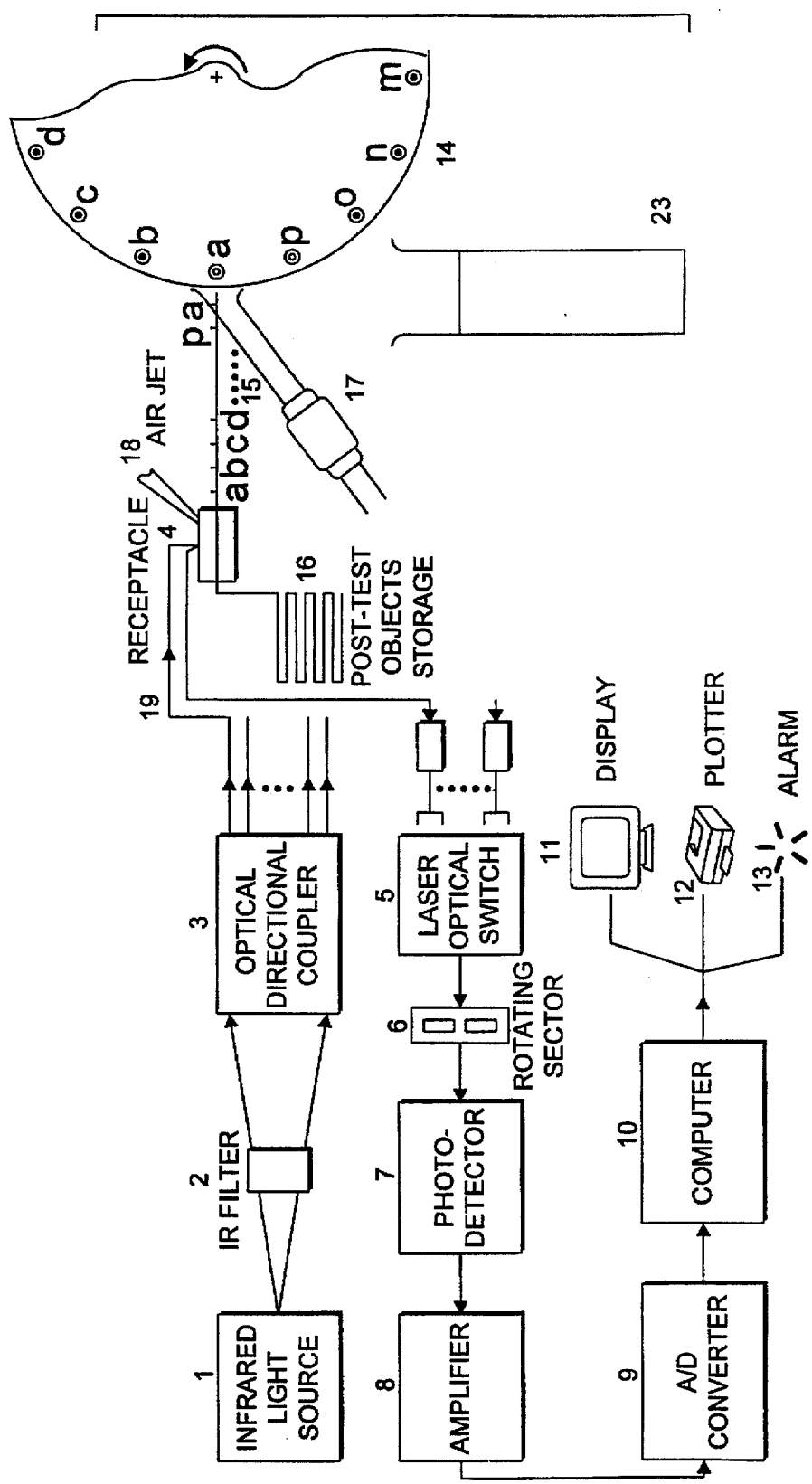
FIG. 1 is a representative view of an automatic non-destructive near infrared spectroscopic machine in accordance with this invention.
Figure 2B:
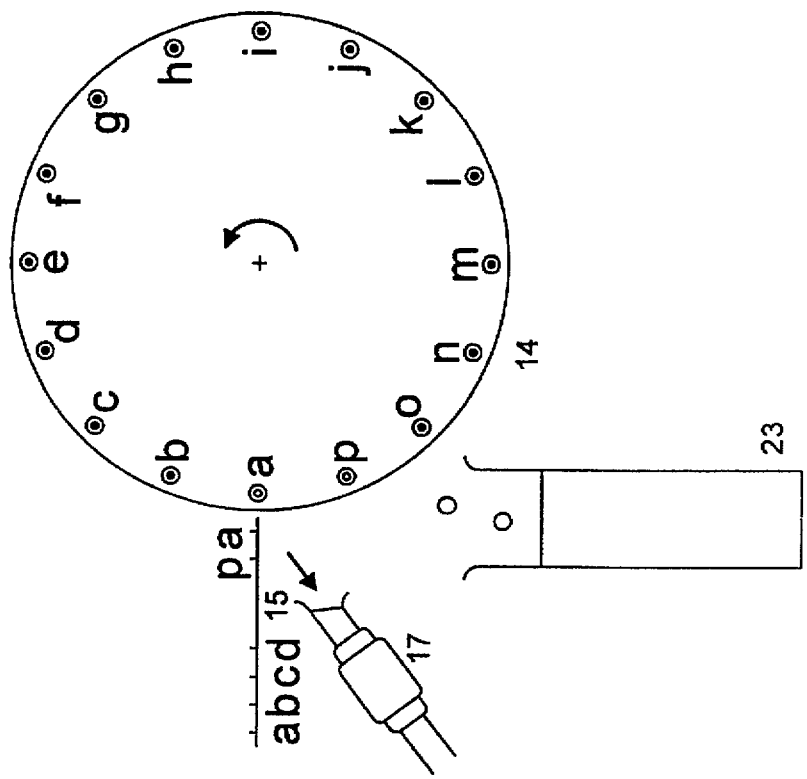
FIG. 2b is a top plan view of a portion of the system shown in FIG. 1 during deactuation away from the supply station which permits the tablets to fall into a holding drum.
Figure 2A:
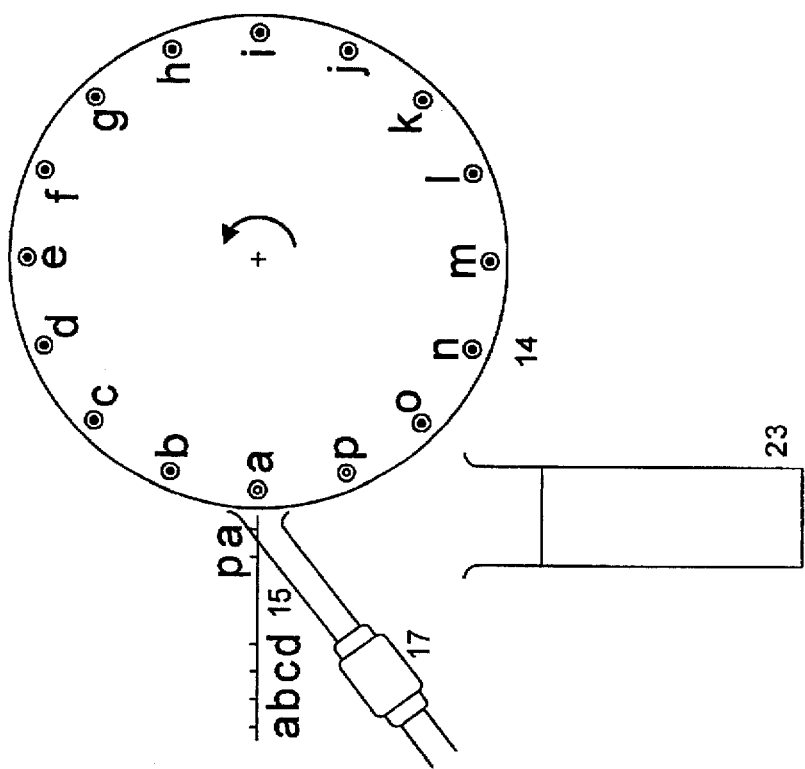
FIG. 2a is a top plan view of a portion of the system shown in FIG. 1 during actuation of the diversion of the tablet from the supply station to the tablet delivery mechanism leading to the receptacle of the infrared fiber optics sensor.
Figure 5:
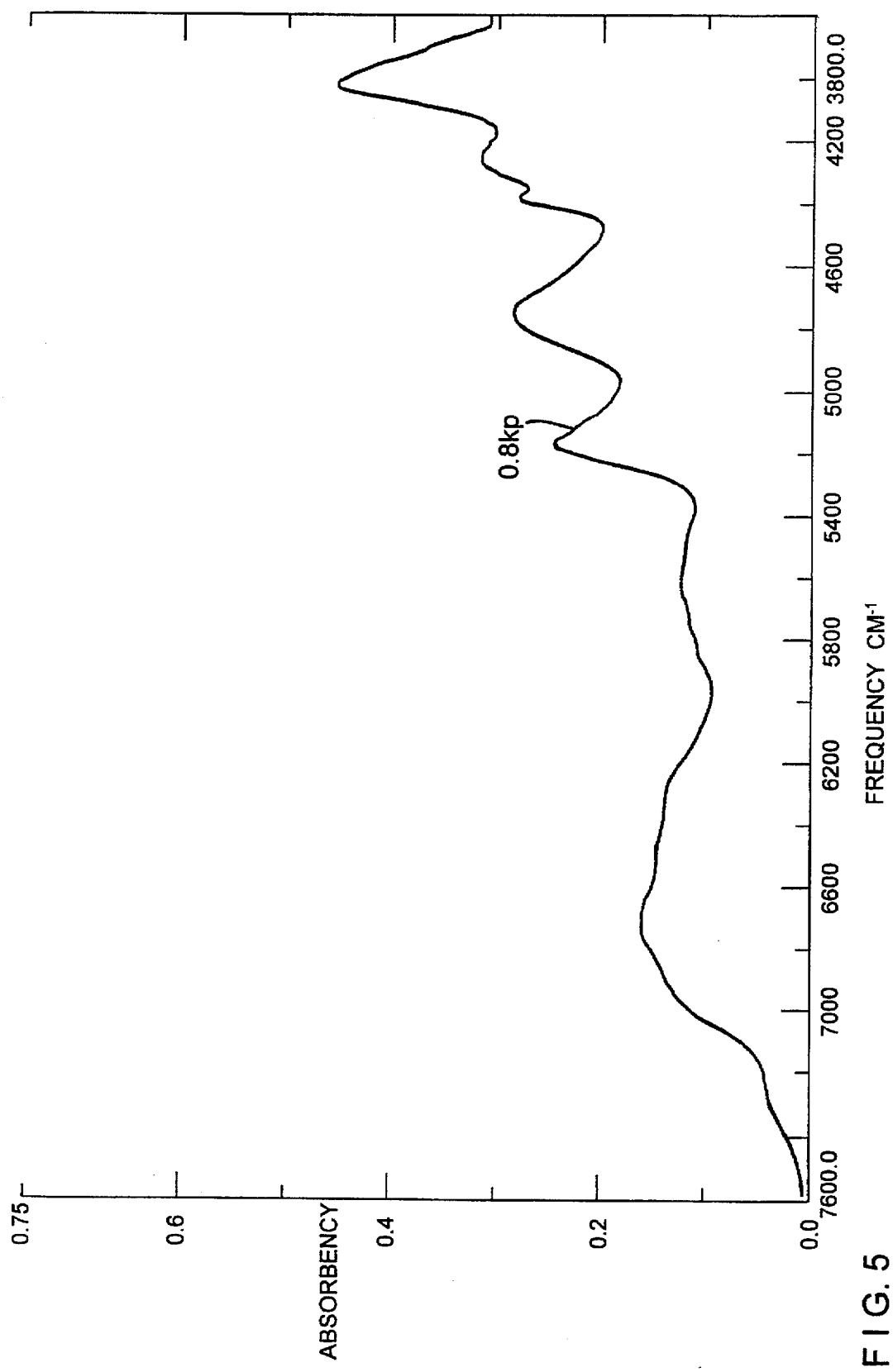
FIG. 5 shows the near infrared absorption spectrum for a tablet, of a certain product, with known hardness of 0.8 kp.
Figure 6:
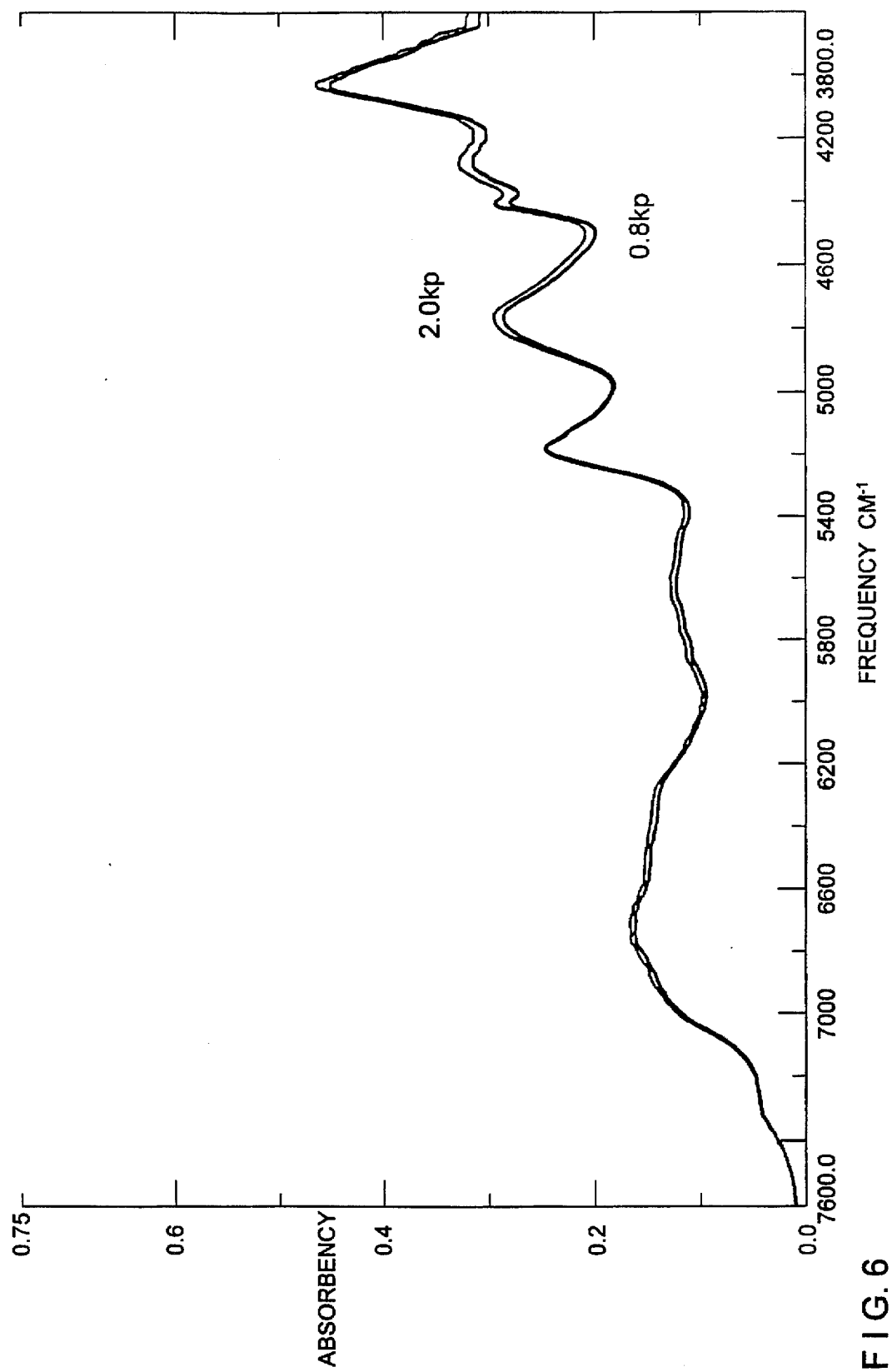
FIG. 6 shows superimposed near infrared absorption spectra for two tablets of known hardness of 0.8 kp and 2.0 kp of the said product in FIG. 5.
Figure 7:
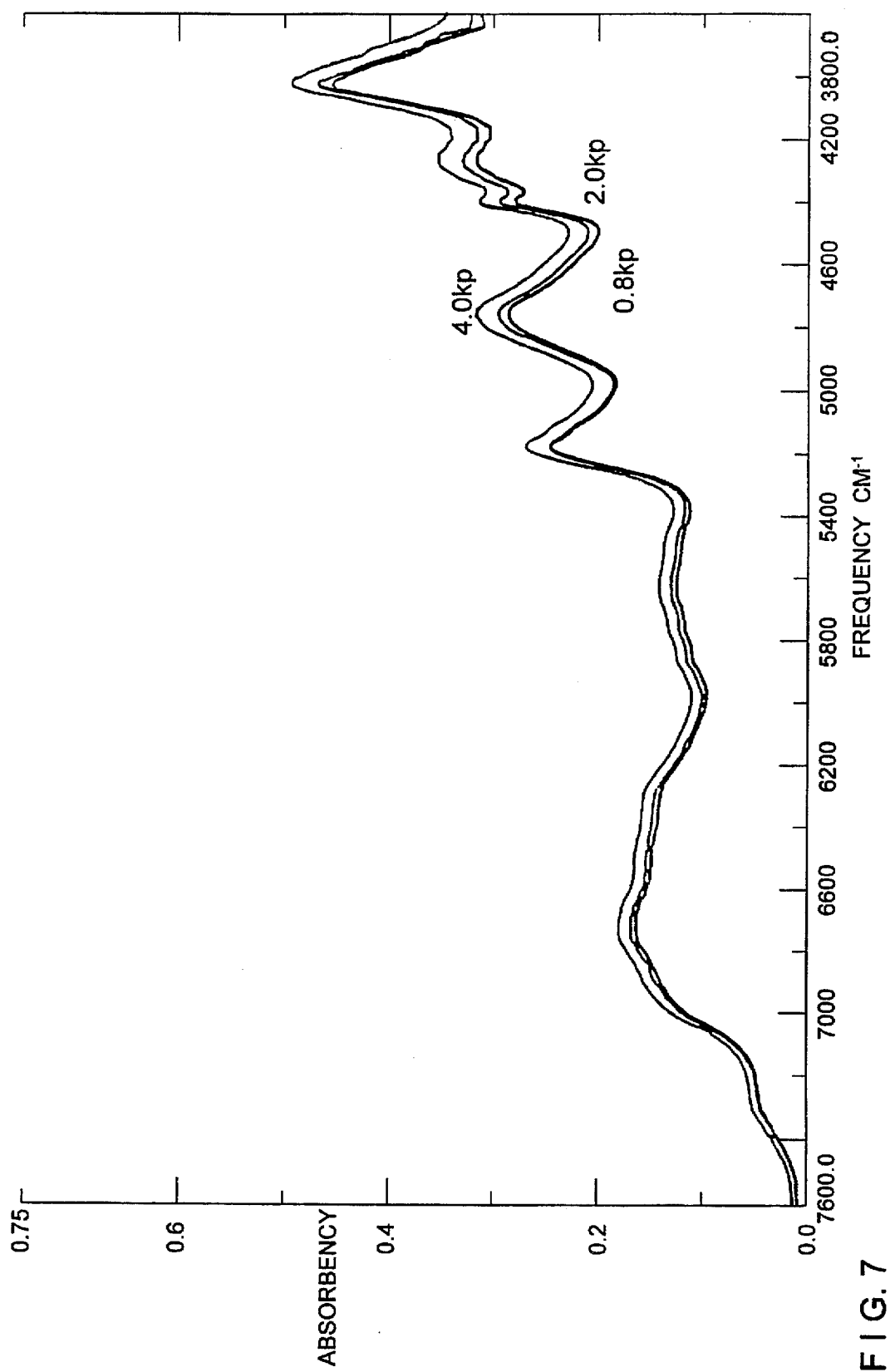
FIG. 7 shows superimposed near infrared absorption spectra for three tablets of known hardness of 0.8 kp, 2.0 kp, and 4.0 kp of the said product in FIG. 5.
Figure 8:
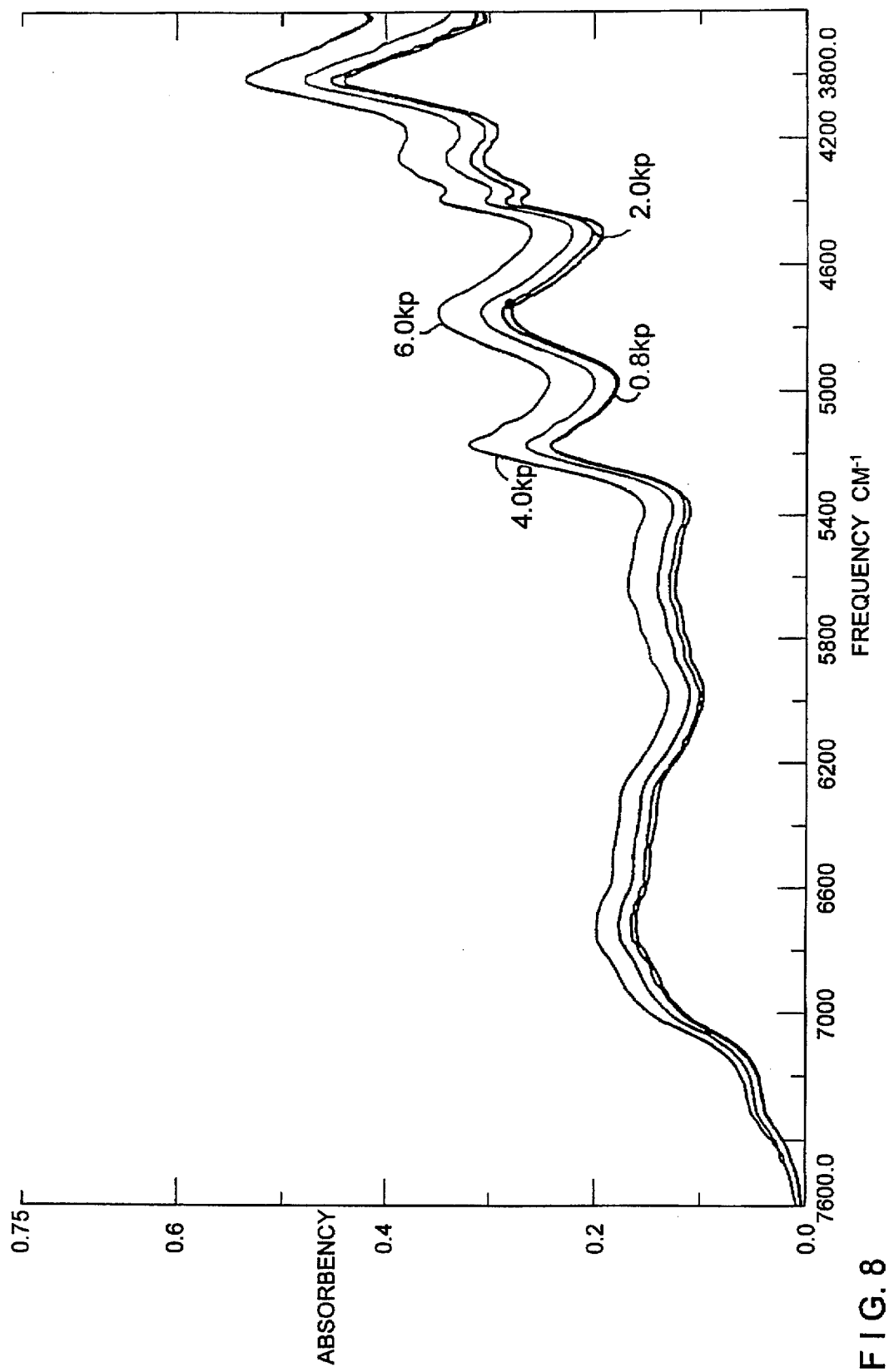
FIG. 8 shows superimposed near infrared absorption spectra of four tablets of known hardness of 0.8 kp, 2.0 kp, 4.0 kp, and 6.0 kp of the said product in FIG. 5.
Figure 9:
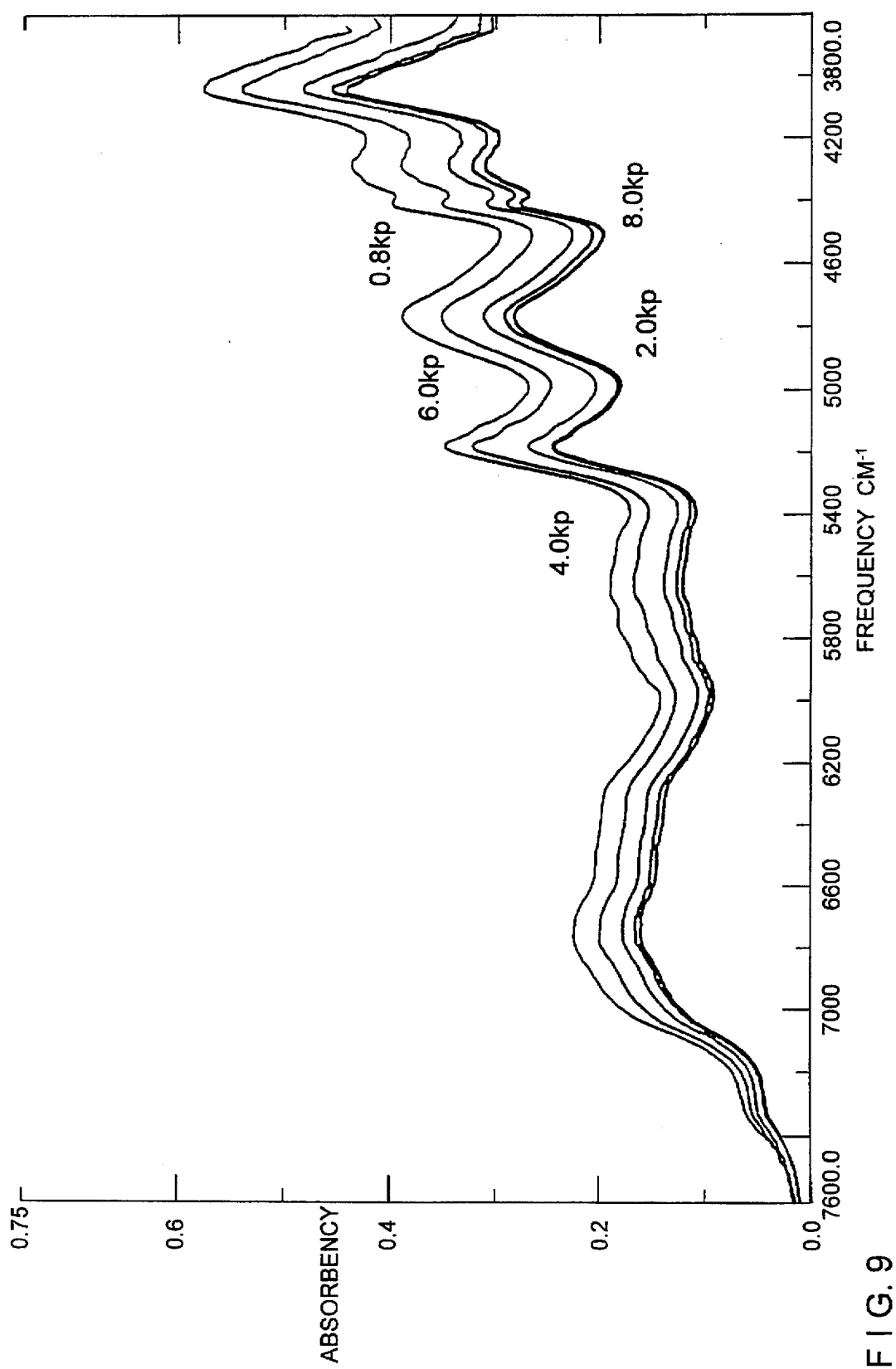
FIG. 9 shows superimposed near infrared absorption spectra of five tablets of known hardness of 0.8 kp, 2.0 kp, 4.0 kp, 6.0 kp, and 8.0 kp of the said product in FIG. 5.
Figure 10:
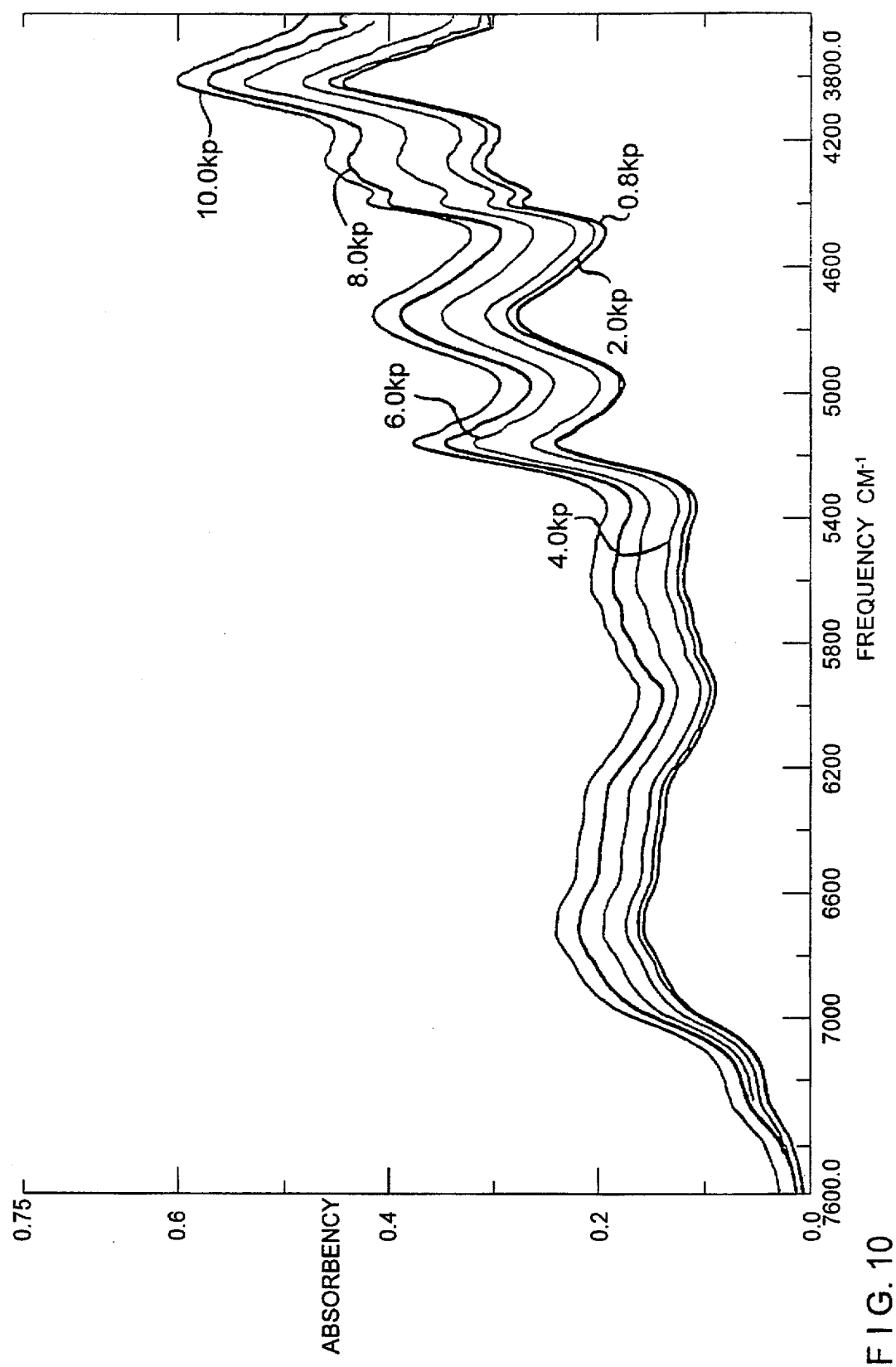
FIG. 10 shows superimposed near infrared absorption spectra of six tablets of known hardness of 0.8 kp, 2.0 kp, 4.0 kp, 6.0 kp, 8.0 kp, and 10.0 kp of the said product in FIG. 5.

The present invention is directed to an automatic non-destructive infrared system which is capable of determining dissolution in mass production operation by measuring the hardness of organic-base objects. Such measurements could be applied to any solid organic-base compound and have a particular utility for being applied to solids such as tablets used in the pharmaceutical industry. The general operation of the system is illustrated in FIG. 1. As shown therein, the system includes a supply of station 14 which is made of a continuous indexing machine of tablet pressing cavities a, b, c, d . . . , p made of any suitable shape such as round, spherical, triangular, diamond, rectangular, square, hexagonal, etc.. Each indexing machine may contain in excess of 356 cavities. From the supply station 14 tablets normally fall into holding reservoir 23. From the supply station 14 samples of pressed tablets are directed by actuator 17, when energized, to conveyor 15 to be automatically detached from conveyor 15 to receptacle 4 through air jet 18. From the supply station 14 actuator 17 is intermittently activated to direct each sample tablet to conveyor 15 maintaining the exact departing sequence of FIG. 2a. Actuator 17 is retracted when samples are not needed and the actual production is directed to holding drum 23 of FIG. 2b.

Conveyor 15 delivers each sample tablet assisted by the air jet 18 to lower parts 21 of receptacle 4, which is automatically opened to contain one tablet sample at a time as in FIG. 3. The infrared fiber optics sensor 19 is firmly attached to upper plate 20 of receptacle 4 in FIG. 4. Infrared fiber optics sensor 19 is aimed at the sample tablet 22 inside receptacle 4, which is supported by lower parts 21. Tablet 22 inside receptacle 4 is spectrophotoscopically analyzed during a certain period of time to measure dissolution and obtain specific identity. When completed, the lower parts 21 of receptacle 4 are automatically opened and the air jet 18 again directs the tested sample 22 to enter the pest-test objects storage station 16, maintaining the same sequence maintained during the departure from the supply station 14.

The sample tablet 22 in receptacle 4 receives pulsated near infrared light waves through infrared fiber optics sensor 19 which receives its generated waves from optical directional coupler 3. Optical directional coupler 3 contains multiple coupled channels feeding infrared light waves through several cables of infrared fiber optics to permit sequential analyses of multiple sample tablets. The Optical directional coupler 3 receives its pulsated near infrared light waves through infrared filter 2.

The near infrared filter 2 filters light wave lengths, permitting only near infrared light waves to flow to the optical directional coupler 3. The infrared light source 1 is a halogen lamp generating light wave lengths which are directed to the infrared filter 2.

The fiber optics infrared cable 19 contains two branches permitting near infrared light waves to travel from one of its branches to sample tablet 22 in receptacle 4, while the other branch of the near infrared fiber optics cable 19 carries reflected light waves from sample tablet 22 in receptacle 4 to LASER optical switch 5, creating interference effect by separating the incoming beam into two parts, then introducing a path difference and finally recombining the beam, generating specific time recording of interferometric pulsated light waves ranging from 700 nm to 2450 nm infrared spectra.

The rotating sector 6 synchronizes reflected interferometric pulsated light waves of the same wave lengths of the same spectrum of both the sample tablet 22 and a comparative standard object selected prior to test procedure. The rotating sector 6 directs the synchronized reflected interferometric pulsated light waves to the photo-detector 7. The resulting beam intensity recorded as a function of optical path difference with infrared sensitive detector is called an interferogram.

The photo-detector 7 measures the reflected intensity of near infrared light waves of sample tablet 22. The photo-detector 7, in the same manner, has previously measured the reflected intensity of near infrared light waves for the known standard object for comparison to sample tablets prior to sending the sample tablets a, b, c, d . . . , p to receptacle 4.

The intensity of the near infrared light waves aimed at each tablet sample 22 through the sending branch of the fiber optics cable 19, entering receptacle 4, is greater than the intensity of the near infrared light waves of the fiber optics cable branch 19 exiting receptacle 4 by the amount of infrared light waves absorbed by the sample tablet 22.

The said photo-detector 7 measures intensity of near infrared light waves in analog form and sends the measurements to amplifier 8.

The amplifier 8 proportionally amplifies the received analog measurements sent by photo-detector 7. The amplifier 8 sends the proportionally amplified measurements to the analog/digital converter 9.

The analog/digital converter 9 converts the proportionally measured analog measurements into corresponding proportionally digital measurements suitable for computer 10.

Computer 10 computing the Fourier transformation of the interferogram yields the infrared spectrum. Computer 10 mathematically divides the known measurements of the standard object by each measurement of the sample tablets 22. The said computer 10 records the data in its resident memory and applies Fourier transformation analysis of the relative reflectance or absorbency of every sample tablet as compared to the known standard object to obtain the near infrared spectrum for each tablet. The near infrared spectra generated by computer 10 are displayed on display monitor 11, and plotted on an electromechanical plotter 12.

Alarm 13 is automatically energized to cause the supply station 14 to take an instantaneous corrective action.

A significant part of this invention is the mathematical integrations of the absorbency values found for each sample tablet 22 extended throughout the entire span of each spectrum achieved at computer 10. This mathematical integration is equivalent to the area of each spectrum for each sample tablet 22. The area also can be used as a functional measure of the energy absorbed by sample tablet 22. The outcome is therefore a single value representing a distinctive measure of sample tablet hardness. Since hardness is the measure dissolution, it is evident that measuring hardness is measuring also dissolution. The details of illustrating the integrated area for each spectrum are best shown in FIGS. 5-10 and FIGS. 12-15. This integration permits the system FIG. 1 to obtain a single value of hardness (dissolution) for each tested sample tablet as a measure of the ability of the supply station 14 to produce products with desired hardness (dissolution).

The integration permits the supply station 14 to take corrective action of tablet production instantaneously, whereas the current industry method of measuring hardness (dissolution) may provide the supply station with an indication of its status within a few hours, leading to the destruction of tablets produced if the hardness (dissolution) is unacceptable.

Figure 11:
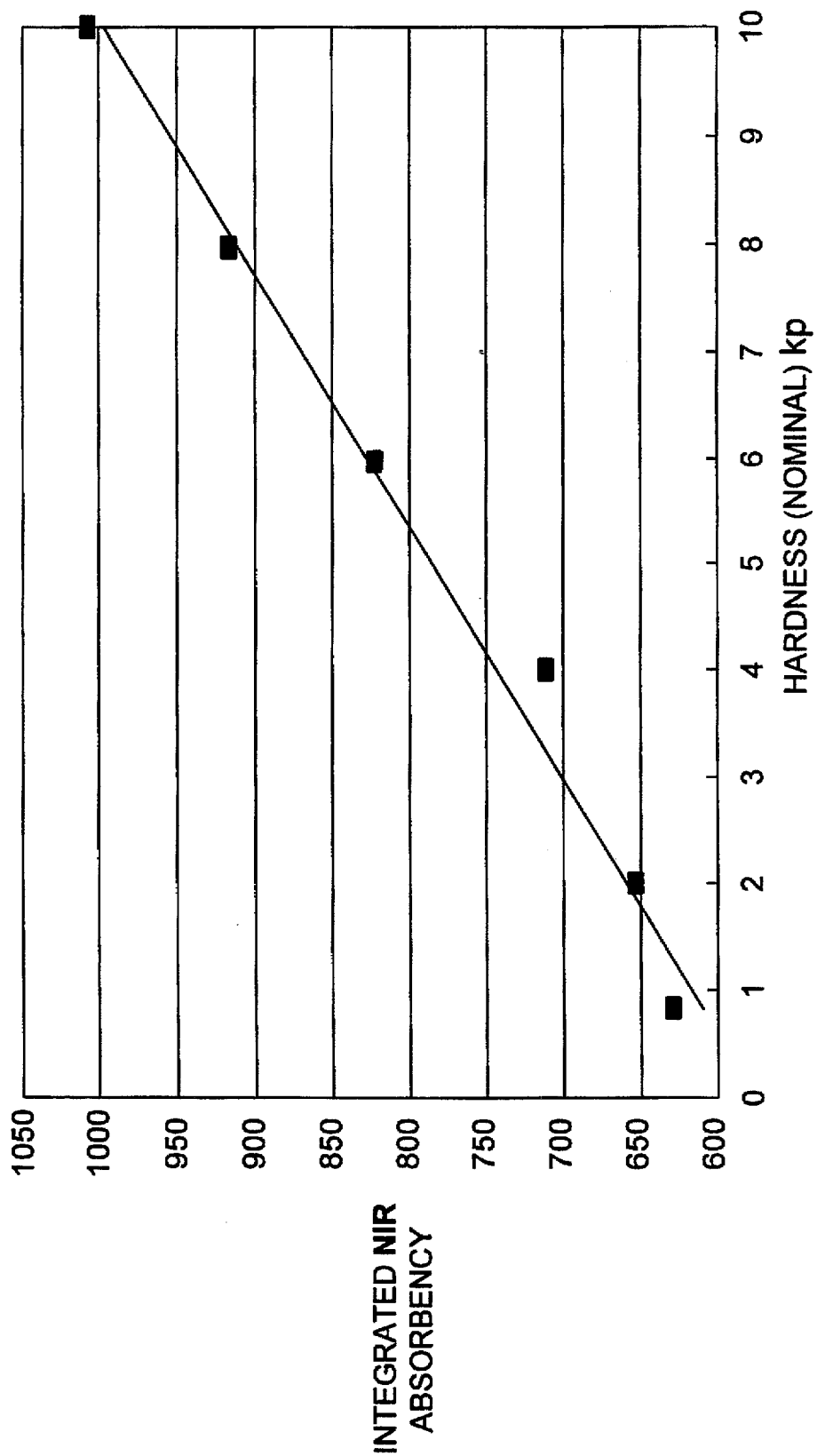
FIG. 11 shows the linear correlation between the integrated near infrared absorbency of each of the six tablets in FIG. 10 and their nominal hardness.
Figure 12:
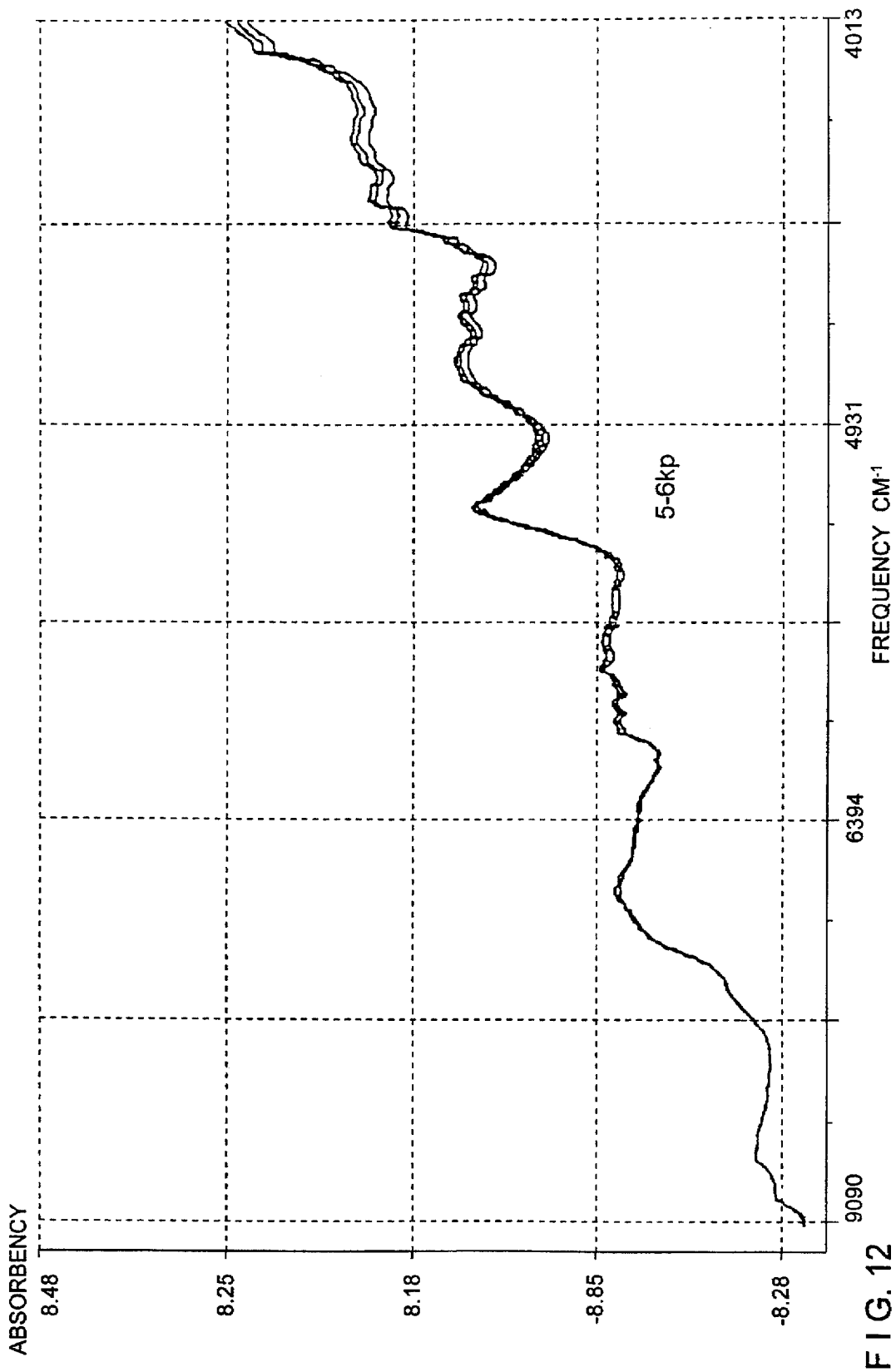
FIG. 12 shows a stack of superimposed near infrared absorption spectra of a set of four tablets, of known hardness ranging from 5.0 kp to 6.0 kp, of a certain product different from the said product in FIG. 5.
Figure 13:
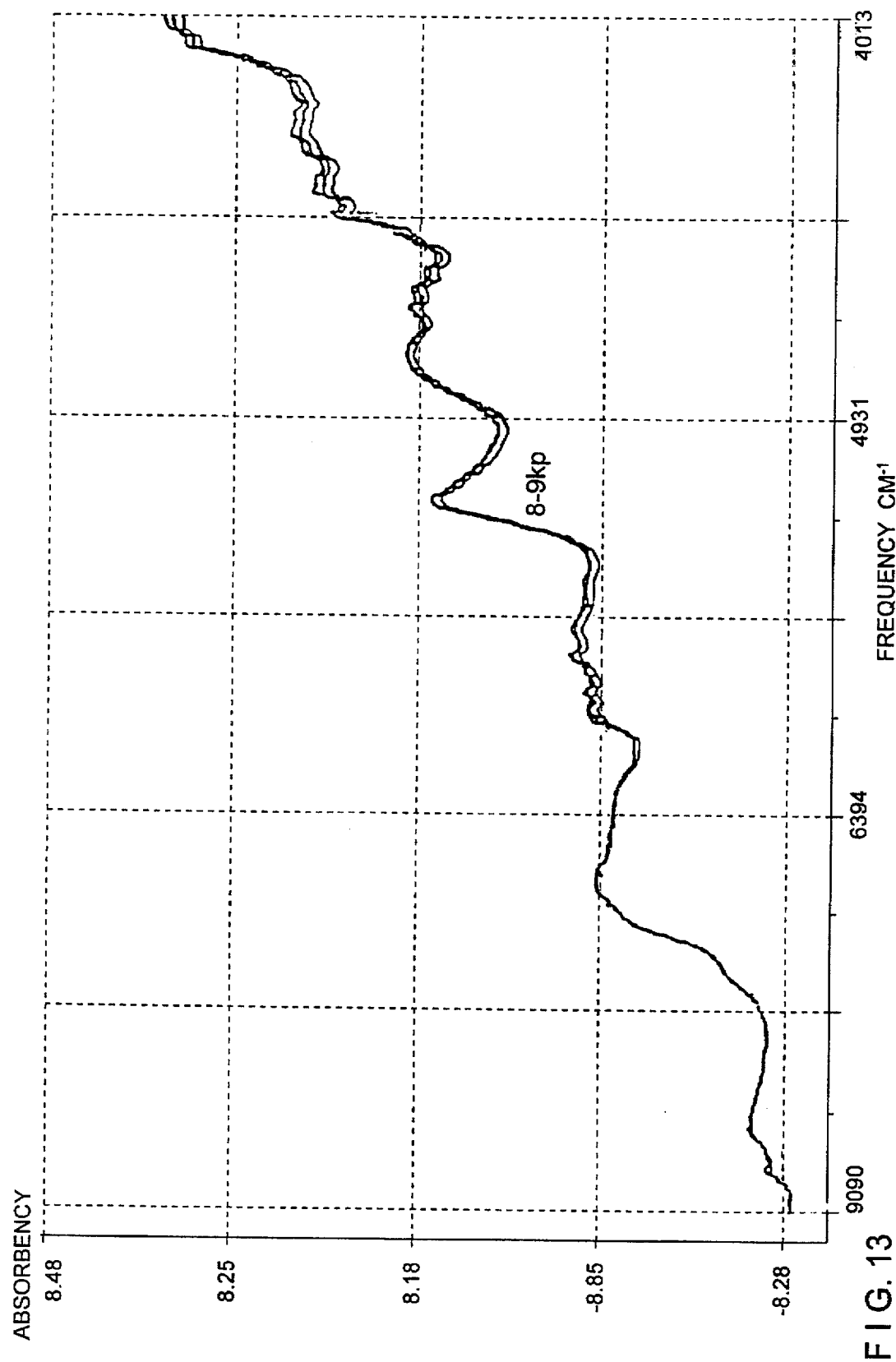
FIG. 13 shows a stack of superimposed near infrared absorption spectra of a set of four tablets, of known hardness ranging from 8.0 kp to 9.0 kp, of the said product in FIG. 12.
Figure 14:
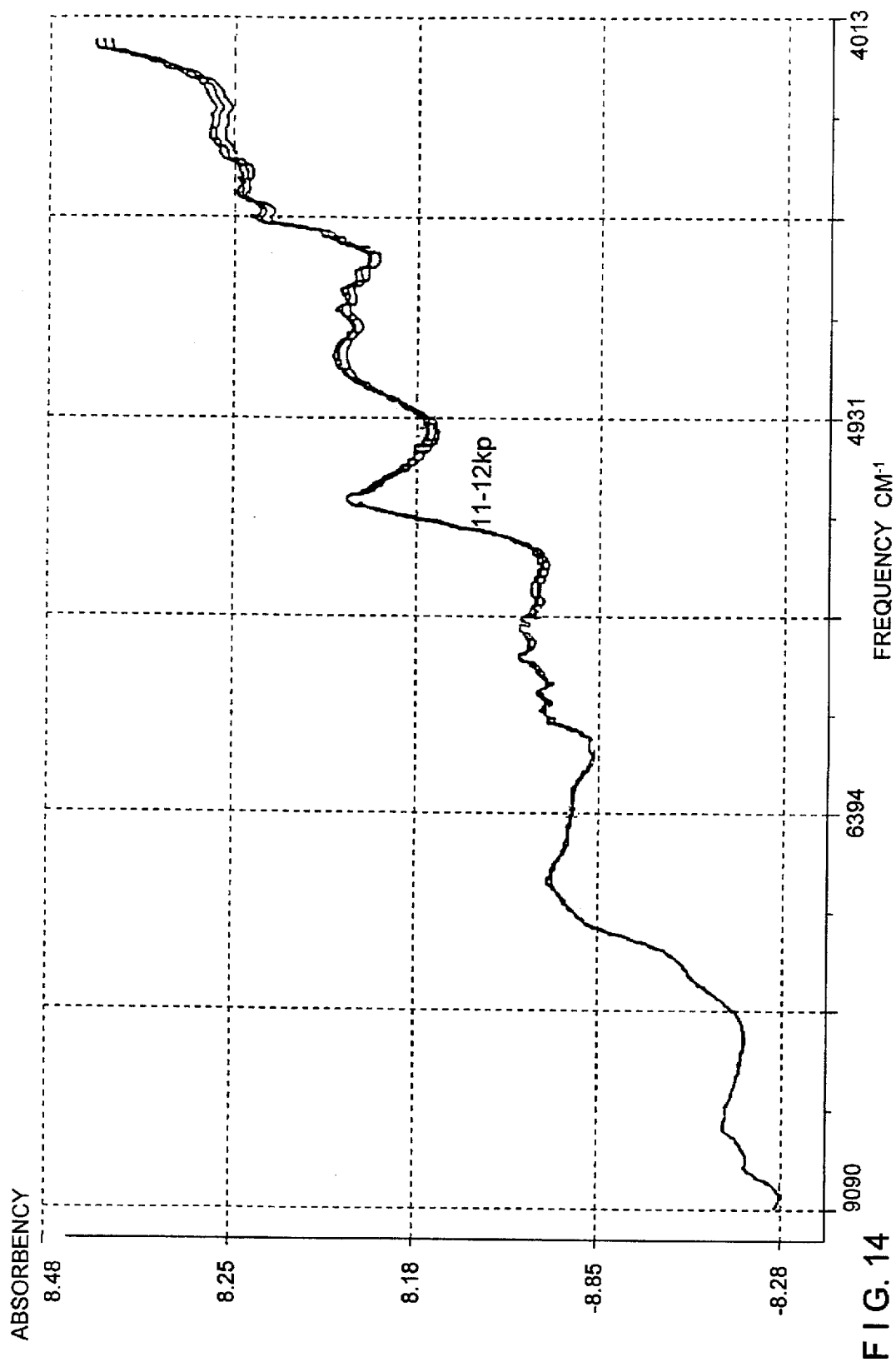
FIG. 14 shows a stack of supedmpesed near infrared absorption spectra of a set of four tablets, of known hardness ranging from 11.0 kp to 12.0 kp, of the said product in FIG. 12.
Figure 15:
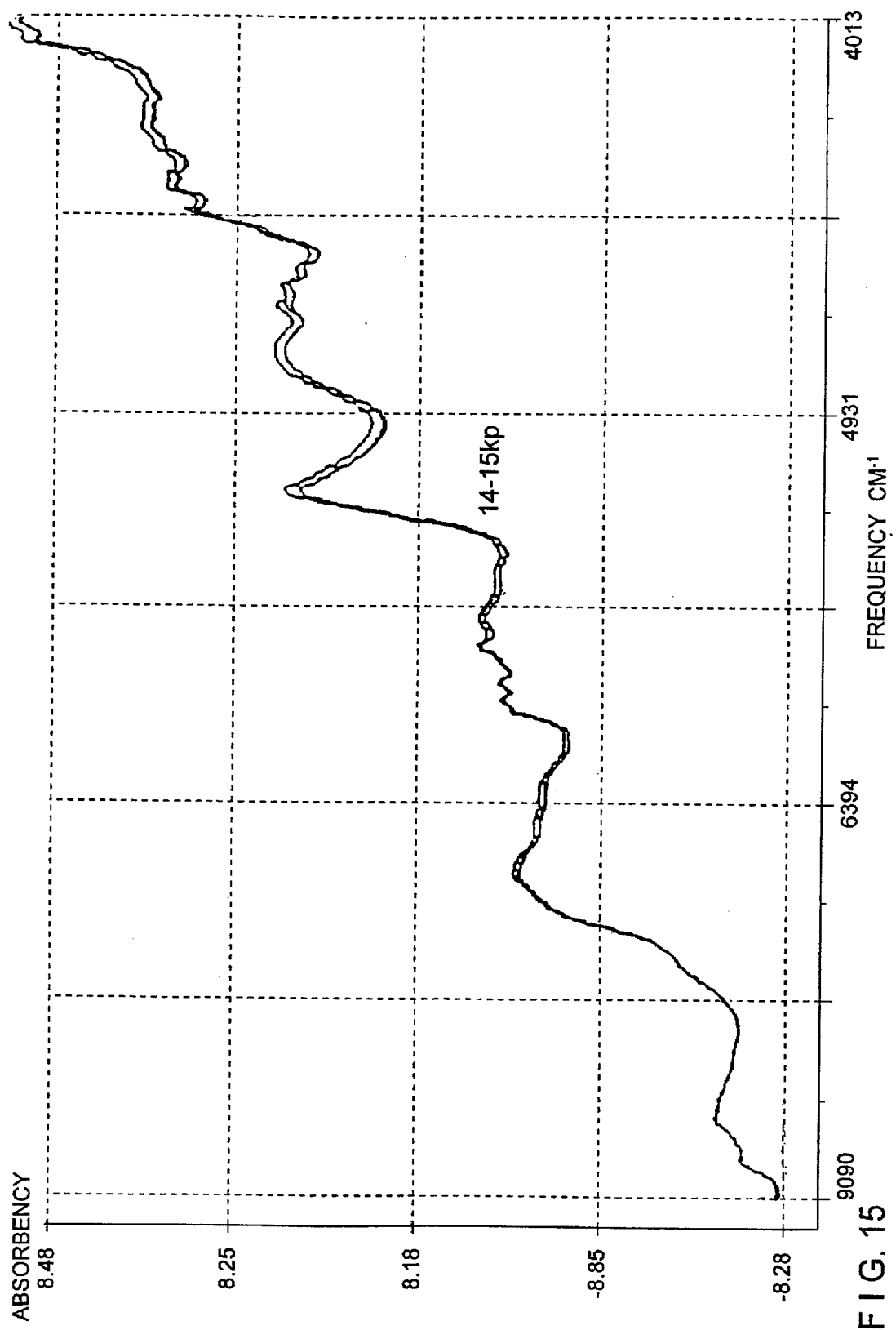
FIG. 15 shows a stack of superimposed near infrared absorption spectra of a set of four tablets, of known hardness ranging from 14.0 kp to 15.0 kp, of said product in FIG. 12.
Figure 16:
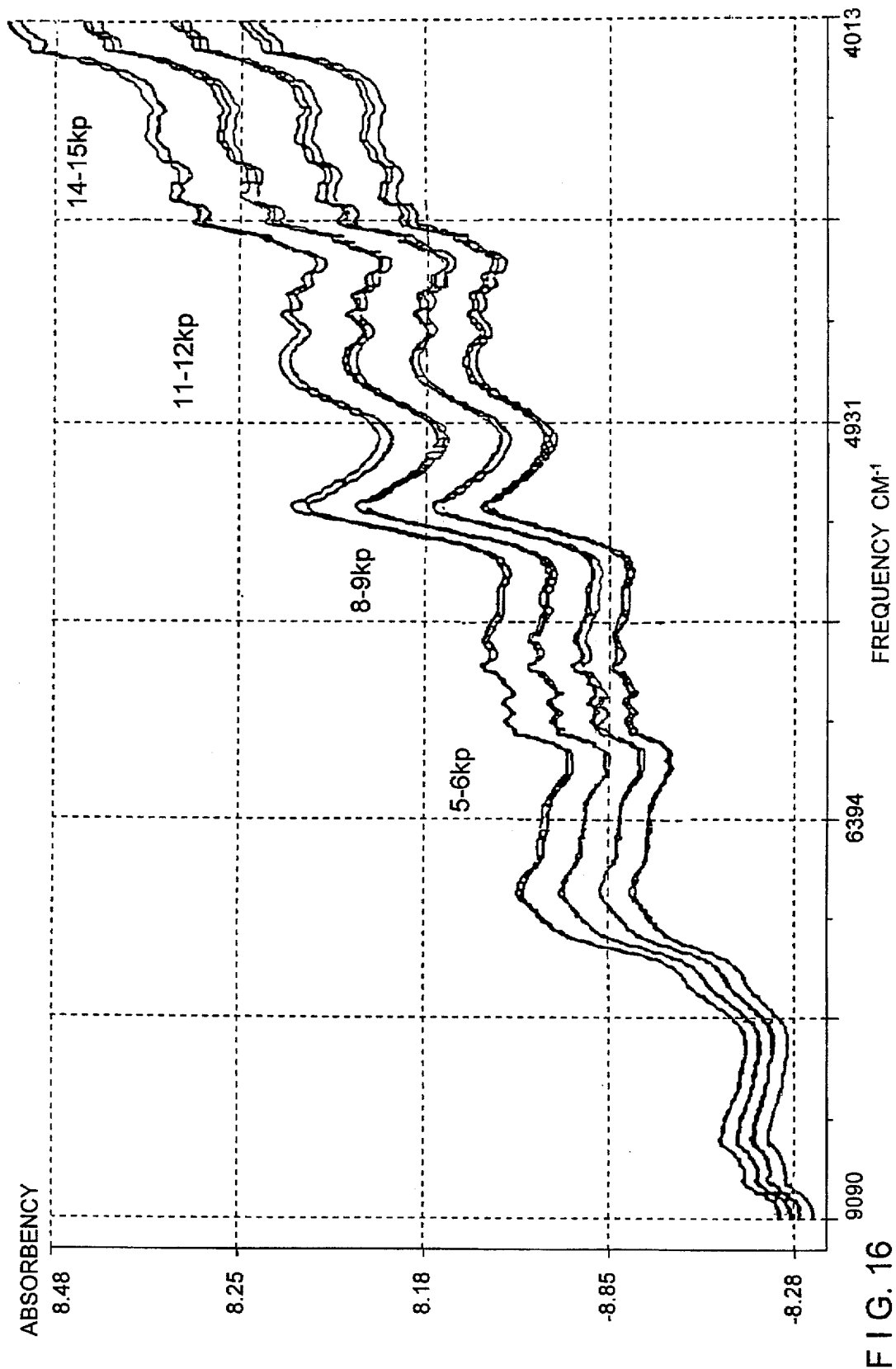
FIG. 16 shows a superimposed stack of the near infrared absorption spectra of each set of tablets in FIGS. 12, 13, 14, and 15.
Figure 17:
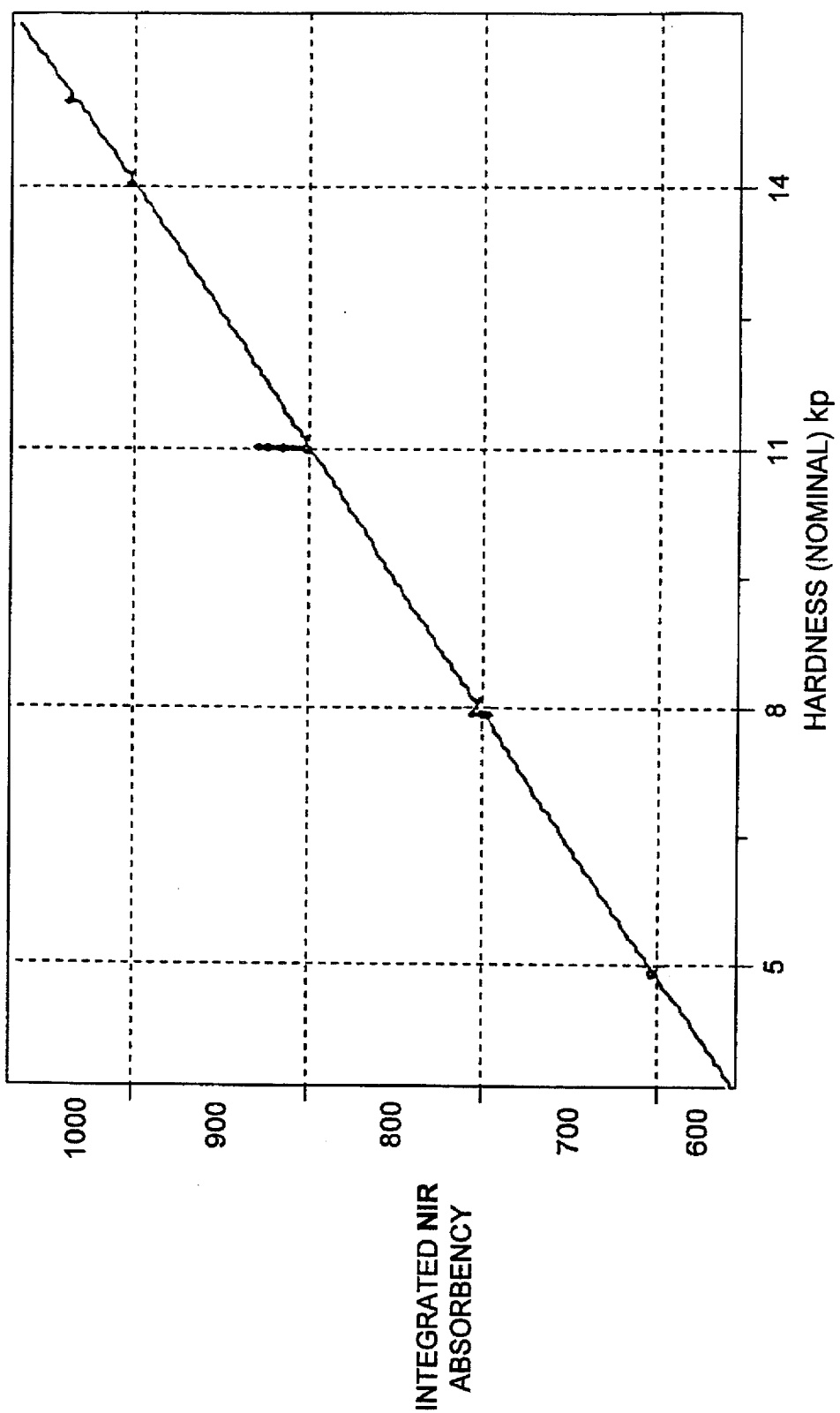
FIG. 17 shows the linear correlation between the integrated near infrared absorbency of each of the four sets of tablets in FIG. 16 and their nominal hardness.

An additional significant part of this invention showed in FIG. 11 and FIG. 16 is the discovery of the straight line correlation between the corresponding integrated area of each tablet spectrum and its actual hardness (dissolution). This discovery provides predictive data of the behavior of organic-base objects that are made of the same chemical compounds and produced under the same conditions to interpolate and extrapolate the necessary data for practical applications.

A further feature of this invention is the critical ability to discriminate between similar products, including their chemical contents and the dosages of the essential elements required to produce the product. Additionally, the tablet can be interrogated to obtain accurate data of the presence or absence of foreign objects important to the safety of the public.

Advantageously, system FIG. 1 operates without the need for time consuming chemical analyses or destruction of sample tablets to measure hardness (dissolution). In practice, the integrated value of each spectrum of each sample tablet is displayed on computer display 11, indicating the hardness (dissolution) value which must be within acceptable upper and lower tolerance control limits which are also displayed on computer display 11.

In the illustrated embodiment, sample tablet 22 is shown as a round-shaped object. Other shapes of organic-base objects may be used whereupon the lower parts of receptacle 4 are adapted to contain the sample object shapes.

In the illustrated embodiment, receptacle 4 is illustrated as an automatic container that is opened at a specific instant to accommodate sample tablet 22, whereupon sample tablet 22 may be placed on a transporting mechanism to be passed directly under the field of view of cable 19.

A further feature of system FIG. 1 is the inclusion of alarm devices 13 disposed at suitable locations for the sensing of the rate of increase of sample tablet hardness to an unacceptable level. The alarm devices may be directly interlocked with the supply station 14.

The invention may be practiced with various modifications. For example, FIG. 3 illustrates an arrangement wherein a single sample tablet 22 is situated in receptacle 4. Multiple sample tablets can be situated and arranged in a suitable receptacle. Additionally, supply station 14 can direct the produced objects to be placed under multiple cables to test all objects produced without the necessity of receptacle 4.

It is to be understood that the above description is intended to exemplify the practice of the invention and may be varied without departing from the concepts of the invention. For example, the invention has been described wherein each sample tablet is disposed to its appropriate location at receptacle 4 assisted by air jet 18. Other manners of conveying the sample tablet may also be used including a miniature robotic mechanism. Also, the post-test objects storage may be replaced by a multiple disc mechanism wherein each disc contains many cavities. Each disc is loaded automatically by a miniature robot. Once all cavities of each disc are filled the disc is dropped downward, allowing a fresh disc containing multiple cavities to replace the filled one. Similarly, the actuator 17 may be replaced by a robotic mechanism to load tablet samples from supply station 14 to receptacle 4, and unload tested sample tablets from receptacle 4 to post-test objects storage 16. The upper plate 20 of said receptacle 4 is either fixed as tablet objects are conveyed to receptacle 4 or movable as tablet objects are not conveyed to said receptacle 4. The lower parts 21 of the receptacle 4 can be removed to facilitate conveying the upper plate 20 carrying the fiber optics cable 19 to the field of view of the tablet objects.

What is claimed is:

1. An automatic non-destructive near infrared system comprising a continuous supply of tablets loaded on a conveyor via an actuator mechanism maintaining a sequence of said tablets on said conveyor, a receptacle comprising an upper plate holding a bundle of at least one fiber optic cable receiving infrared waves from an opto-directional coupler, conveying near infrared light waves, said receptacle further comprising a pair of lower parts accommodating presence of objects, an air jet means for directing the objects to rest at said receptacle and to depart from said receptacle, said tablets departing from receptacle are arranged in storage maintaining said sequence, said bundle of at least one fiber optic cable carrying upstream and downstream layers of fiber optics, said upstream cable layers feeding infrared waves and said downstream cable layers conveying reflected infrared waves to an optical switch means, a means for conveying and amplifying data received from said downstream cable layers to an infrared spectrophotometer to a computer and further conveyed by electronic means to a computer display monitor displaying status of said tablets in Fourier Transformation form, said Fourier Transformation form is integrated and conveyed to a plotter comprising two directional motions responding to said computer output drafting the status of said spectrum, an output of integration of said Fourier Transformation form is further conveyed to an alarm means declaring a status of said tablets, said alarm means comprising sensorial information conveyed to a supply means of tablets, said output of integration of said Fourier Transformation form yields linear phenomena conveyed to said plotter and said computer display plots integrated absorbency in a first direction and nominal hardness (dissolution) of the tablets in a second direction perpendicular to said first direction.

2. The system of claim 1, wherein continuous supply of tablet objects loaded on a conveyor via an actuator mechanism electro-pneumatically actuated, and said actuator mechanism comprising electro-pneumatic solenoid actuating devices.

3. The system of claim 2, wherein said conveyor includes a plurality of cavities and wherein said continuous supply of tablets loaded on said conveyor via an actuator mechanism is synchronized between each of said plurality of cavities and its corresponding tablet placed onto conveyor.

4. The system of claim 3, wherein said conveyor maintains a departing sequence of said tablets from said actuator.

5. The system of claim 1, wherein said air jet means for directing the objects is an electro-pneumatic solenoid device actuated to maintain an orderly sequence of said tablets.

6. The system of claim 1, wherein said receptacle comprising an upper plate holding bundle of fiber optics cable or plurality of fiber optics cables, said receptacle upper plate is fixed where tablet objects are conveyed to said receptacle.

7. The system of claim 1, wherein said receptacle comprising of an upper plate holding a bundle of fiber optics cable or plurality of fiber optics cables, said receptacle upper plate is movable where tablet objects are not conveyed to said receptacle.

8. The system of claim 1, wherein said pair of lower pads accommodating presence of objects is automatically actuated.

9. The system of claim 1, wherein said bundle of fiber optics cable or plurality of fiber optics cables carrying dual layers of fiber optics of upstream cable layers feeding infrared waves and downstream cable layers conveying reflected infrared waves, combine in a unified bundle at the point of entering said receptacle, while downstream cable layers separates after departing said receptacle.

10. The system of claim 1, wherein said means of conveying and amplifying data received from said downstream fiber optics cable or plurality of cables to said infrared spectrophotometer to computer, includes means of conducting multiple parallel processing of all spectra corresponding to tablet objects.

11. The system of claim 1, wherein said means of conveying and amplifying data received from said downstream fiber optics cable or plurality of cables to said infrared spectrophotometer to computer, includes means of sequencing and storing data for sequential processing of all spectra corresponding to tablet objects.

12. The system of claim 1, wherein said computer computes mathematical integration in an output form for each spectrum generated by said spectrophotometer, resulting in a single value for each spectrum of the tablet object.

13. The system of claim 12, wherein said resulting single value for each spectrum of the tablet object is measured against two predetermined tolerance values, one representing an upper acceptable value and the other representing a lower acceptable value, determining the acceptability of the tablet hardness (dissolution).

14. The system of claim 1, wherein said output form is conveyed by electronic means to computer display monitor includes an electronic mechanism sequencing the data of each stored spectrum, arranging the hardness (dissolution) data in the proper sequence.

15. The system of claim 14, wherein said electronic means includes a video recording means.

16. The system of claim 1, wherein said computer output form is integrated and conveyed to a plotter which responsive to said computer drafts the status of said spectrum, said computer output form in a three dimensional illustrating an absorbency distribution.

17. The system of claim 1, wherein said alarm means includes means for stopping the supply station.

18. An apparatus comprising:
means for exposing a sample to a plurality of light beams of varying wavelengths thereby creating a plurality of reflected light beams;
means for measuring intensities of said plurality of reflected light beams and further generating a spectrum of relative reflectance or absorbance of said plurality of reflected light beams by the sample;
means for performing a Fourier transform on said spectrum; and
means for integrating output of said means for performing a Fourier transform thereby determining hardness of the sample.

19. A method comprising the steps of:
exposing a sample to a plurality of light beams of varying wavelengths thereby creating a plurality of reflected light beams;
measuring intensities of said plurality of reflected light beams and further generating a spectrum of relative reflectance or absorbance of said plurality of reflected light beams by the sample;
performing a Fourier transform on said spectrum; and
integrating output of said step of performing a Fourier transform thereby determining hardness of the sample.

20. An apparatus comprising:
means for exposing a sample to a plurality of light beams of varying wavelengths thereby creating a plurality of reflected light beams;
means for measuring intensities of said plurality of reflected light beams and further generating a spectrum of relative reflectance or absorbance of said plurality of reflected light beams by the sample;
means for performing a Fourier transform on said spectrum; and
means for integrating output of said means for performing a Fourier transform thereby determining contents of the sample.

21. A method comprising the steps of:
exposing a sample to a plurality of light beams of varying wavelengths thereby creating a plurality of reflected light beams;
measuring intensities of said plurality of reflected light beams and further generating a spectrum of relative reflectance or absorbance of said plurality of reflected light beams by the sample;
performing a Fourier transform on said spectrum; and
integrating output of said step of performing a Fourier transform thereby determining contents of the sample.

* * * * *